(12) United States Patent
Liu et al.

(10) Patent No.: US 10,533,944 B2
(45) Date of Patent: Jan. 14, 2020

(54) METHOD FOR DETERMINING MATURITY IN OIL SOURCE ROCK BY TOTAL SCANNING FLUORESCENCE AND THE DEVICE THEREFOR

(71) Applicant: PetroChina Company Limited, Beijing (CN)

(72) Inventors: Keyu Liu, Beijing (CN); Hua Tian, Beijing (CN); Caineng Zou, Beijing (CN); Shuichang Zhang, Beijing (CN); Shaobo Liu, Beijing (CN); Mengjun Zhao, Beijing (CN); Xuesong Lu, Beijing (CN); Junjia Fan, Beijing (CN); Xiuli Li, Beijing (CN); Lili Gui, Beijing (CN); Qingong Zhuo, Beijing (CN); Xingzhi Ma, Beijing (CN); Yanjie Gong, Beijing (CN); Zhichao Yu, Beijing (CN); Qingyang Meng, Beijing (CN)

(73) Assignee: PETROCHINA COMPANY LIMITED, Beijing (CN)

( * ) Notice: Subject to any disclaimer, the term of this patent is extended or adjusted under 35 U.S.C. 154(b) by 0 days.

(21) Appl. No.: 16/170,914

(22) Filed: Oct. 25, 2018

(65) Prior Publication Data

US 2019/0170644 A1 Jun. 6, 2019

(30) Foreign Application Priority Data

Oct. 27, 2017 (CN) .................. 2017 1 10251777

(51) Int. Cl.
*G01N 21/64* (2006.01)
*G01N 33/28* (2006.01)

(52) U.S. Cl.
CPC ....... *G01N 21/645* (2013.01); *G01N 33/2823* (2013.01); *G01N 2021/6417* (2013.01)

(58) Field of Classification Search
CPC ............ G01N 21/645; G01N 33/2823; G01N 2021/6417
(Continued)

(56) References Cited

U.S. PATENT DOCUMENTS 6,080,950 A    6/2000 Jalink

FOREIGN PATENT DOCUMENTS

CN    102253016 A    11/2011
CN    103115908 A    5/2013
(Continued)

OTHER PUBLICATIONS

Liu et al. ,Innovative fluorescence spectroscopic techniques for rapidly characterising oil inclusions, Jul. 2014, Organic Geochemistry vol. 72 pp. 34-45 ; DOI: 10.1016/j.orggeochem.2014.04.010 (Year: 2014).*

(Continued)

*Primary Examiner* — David P Porta
*Assistant Examiner* — Gisselle M Gutierrez
(74) *Attorney, Agent, or Firm* — Foley & Lardner LLP (57) ABSTRACT

A device and method of determining thermal maturity of oil source rocks by total scanning fluorescence including testing the organic solution of the extract from a series of oil source rock samples collected at different depths by total scanning fluorescence; building a model for interpretation of the oil source rock maturity according to the variation with depth of the TSF Intensity parameter and the TSF R1 parameter obtained by total scanning fluorescence, and identifying the stage of initial oil generation, the stage of major oil generation and the stage of major gas generation; and establishing the relationship between the TSF Intensity parameter and/or the TSF R1 parameter with the existing characteristic parameters that quantitatively characterize the maturity of (Continued)

oil source rocks, thereby accomplishing the analysis and determination of the maturity of the oil source rocks.

8 Claims, 5 Drawing Sheets

(58) Field of Classification Search
USPC .......................................................... 250/301
See application file for complete search history.

(56) References Cited

FOREIGN PATENT DOCUMENTS

| | | |
|---|---|---|
| CN | 106323924 A | 1/2017 |
| CN | 106837317 A | 6/2017 |

OTHER PUBLICATIONS

Liu et al., "Quantitative Fluorescence Techniques and Their Applications in Hydrocarbon Accumulation Studies," Earth Science, vol. 41, No. 3, pp. 373-384 (Mar. 2016).

* cited by examiner

METHOD FOR DETERMINING MATURITY IN OIL SOURCE ROCK BY TOTAL SCANNING FLUORESCENCE AND THE DEVICE THEREFOR

CROSS-REFERENCE TO RELATED PATENT APPLICATIONS

This application claims the benefit of and priority to Chinese Patent Application No. 2017110251777, filed Oct. 27, 2017, which is incorporated herein by reference in its entirety.

TECHNICAL FIELD

The present invention relates to the technical field of petroleum exploitation, and in particular, to a method of determining maturity in oil source rocks by total scanning fluorescence (TSF) and the device therefor.

BACKGROUND

At present, the methods for the determining thermal maturity of oil source rocks are mainly classified into two types: one type of method studies the parameters of the evolutionary characteristics of rock kerogens, such as vitrinite reflectance ($R_o$), rock pyrolysis, fluorescence alteration of multiple macerals (FAMM), the degree of spore-pollen carbonization, thermal alteration index (TAI), conodont alteration index (CAI), kerogen elemental composition and the like, which method, despite of relatively high accuracy, has drawbacks such as requirement of large sample amount, complex testing procedures and extended duration; the other studies the parameters of the evolution characteristics of soluble organic substances in oil source rocks, such as carbon preference index (CPI), odd-even predominance (OEP), biomarker compound parameters such as sterane and terpane isomerization ratio, which is mainly used for qualitative evaluation but hardly for quantitative analysis.

Vitrinite reflectance is observed by using the reflectance of organic particles and is closely related to the aromatization and polycondensation of the organic molecules; depending on the refractive index and absorption coefficient, it increases as the double bonds of carbon atoms increase, that is, it increases as the degree of aromatization of vitrinite components increases. The major limitation to vitrinite reflectance is that vitrinite components contribute poorly to the oil generation as compared to the liptinite components, while some source rocks having strong predisposition to oil generation are deficient in or contain very little vitrinite. Therefore, the application of vitrinite reflectance is limited.

SUMMARY

One object of the present invention is to provide a method of determining thermal maturity of oil source rocks by total scanning fluorescence (TSF).

Another object of the present invention is to provide a device for the determining thermal maturity of oil source rocks by total scanning fluorescence.

In order to achieve the above objects, a method of determining thermal maturity of oil source rocks by total scanning fluorescence is provided, including the steps of testing the organic solution of the extract from a series of oil source rock samples collected at different depths by total scanning fluorescence, wherein the concentration of the extract in the organic solution is 0.01 ppm to 1000 ppm, preferably 1 ppm to 100 ppm; and obtaining TSF Intensity parameters and TSF R1 parameters of the total scanning fluorescence spectrum, wherein the TSF Intensity is the value of the maximum fluorescence intensity in the total scanning fluorescence spectrum, and the TSF R1 is the ratio of the intensity at 360 nm to the intensity at 320 nm of the fluorescence spectrum with an emitting light at 270 nm: building a model for interpretation of the oil source rock maturity according to the variation with depth of the TSF Intensity parameter and the TSF R1 parameter obtained by total scanning fluorescence, and identifying the stage of initial oil generation, the stage of major oil generation and the stage of major gas generation; wherein the identification criterion lies in that the initial position of the stage of initial oil generation is set when the increase of the TSF R1 parameter becomes leveling, the initial position of the stage of major oil generation is set when the TSF R1 parameter turns from leveling to decreasing, and the initial position of the stage of major gas generation is set when the TSF Intensity parameter turns from leveling to decreasing; and establishing the relationship between the TSF Intensity parameter and/or the TSF R1 parameter with the existing characteristic parameters that quantitatively characterize the maturity of oil source rocks, thereby accomplishing the analysis and determination of the maturity of the oil source rocks.

With total scanning fluorescence (TSF), an emission spectrum is obtained by scanning with an exciting light of continuously changing wavelengths, and the results can be represented in the form of a three-dimensional or contour line, where the x, y, z coordinates are excitation wavelength (excitation, nm), emission wavelength (emission, nm), and fluorescence intensity (TSF intensity, pc), respectively, which is also known as three-dimensional fluorescence spectroscopy. The inventor found in the study that at certain concentration, the two parameters, TSF Intensity and TSF R1, in total scanning fluorescence spectrum exhibit a certain linear relationship with the maturity of oil source rock extracts. With this specific linear relationship, different stages of oil source rock maturity can be quantitatively identified. Therefore, a method of determining thermal maturity of oil source rocks by total scanning fluorescence is proposed. The method is applicable to a wide range of applications without being limited by the vitrinite content. Moreover, the method is advantageous in terms of usage of less samples, rapid and simple detection, useful in analysis of samples on a large scale, and also suitable for measuring sample maturity outside the visible fluorescence range.

In the above method of determining thermal maturity of oil source rocks by total scanning fluorescence, preferably, the process of establishing the relationship between the TSF Intensity parameter and/or the TSF R1 parameter with the existing characteristic parameters for quantitatively characterize the maturity of oil source rocks includes establishing a calibration curve of the TSF Intensity parameter and/or the TSF R1 parameter restricted by the existing characteristic parameters that quantitatively characterize the maturity of the oil source rocks.

In the above method of determining thermal maturity of oil source rocks by total scanning fluorescence, preferably, the method further includes the step of establishing a database of calibration curves from different regions so that TSF R1 is directly used as the indication of maturity.

In the above method of determining thermal maturity of oil source rocks by total scanning fluorescence, preferably, the existing characteristic parameters that quantitatively characterize the maturity of oil source rocks include vitrinite reflectance, rock pyrolysis, the degree of spore-pollen carbonization, or thermal alteration index. Since the vitrinite reflectance is presently a rather reliable parameter for determining thermal maturity of oil source rocks, it is preferable to establish the relationship between the TSF Intensity parameters and/or the TSF R1 parameters with the vitrinite reflectance.

In the above method of determining thermal maturity of oil source rocks by total scanning fluorescence, for unknown hydrocarbon source rocks (i.e., hydrocarbon source rocks possibly located before the stage of initial oil generation), due to the need of considering both the TSF Intensity and the TSF R1 parameters, while the TSF Intensity parameter may be influenced by the concentration of the extract in the organic solution, a narrower range of solution concentration is to be used, with a preferable concentration as recommended at 1 ppm to 100 ppm. For known hydrocarbon source rocks (i.e., hydrocarbon source rocks already in the stage of initial oil generation, which represents the majority of the analytes), the maturity of the hydrocarbon source rock increases with decrease in the TSF R1 parameter; the TSF R1 parameters can be used for quantitative determination of the maturity after being calibrated using parameters such as $R_0$, without consideration of the TSF Intensity parameter; the concentration of the extract in the organic solution has less influence on the TSF R1 parameter, i.e., a wider range of solution concentration is applicable, e.g. 0.01 ppm to 1000 ppm.

In the above method of determining thermal maturity of oil source rocks by total scanning fluorescence, preferably, the process of preparing the organic solution of the extract includes pulverizing the sample to be tested with the mass of $M_r$, adding the organic solvent, and ultrasonically extracting at least twice; diluting to the preset concentration after extraction to prepare the organic solution of the extract.

In a preferred embodiment, the particular process of preparing the organic solution of the extract is as follows:

(1) obtaining an uncontaminated sample from the sample to be tested, and pulverizing the sample particles to a certain particle size;

(2) selecting 0.1 g-1.0 g rock sample to be measured, with the mass measured as $M_r$, adding 10 mL of organic solvent (including but not limited to dichloromethane), and ultrasonically extracting for 10 minutes;

(3) standing for 10 minutes, and further ultrasonically extracting for 10 minutes;

(4) standing for a certain period of time, and transferring $V_1$ mL (0.001 mL-0.1 mL) into an analysis cuvette (vial), into which 3 mL of organic solvent is added; and (5) placing the analysis cuvette in a fluorescence spectrometer for testing, measuring the TSF Intensity original parameter and TSF R1 parameter of the fluorescence spectrum; and correcting the TSF Intensity original parameter by multiplying by $0.1*3/(M_r \cdot V_1)$ (for normalization, normalizing a concentration of 0.1 g sample dissolved in 10 mL of the organic solvent because the solution is essentially diluted by $3/V_1$ in step 4, and then normalizing $M_r$ to 0.1 g for reversion) to obtain the TSF Intensity parameter.

The present disclosure also provides a device for determining thermal maturity of oil source rocks by total scanning fluorescence, including a first unit for testing by total scanning fluorescence spectroscopy an organic solution of the extract of a series of oil source rock samples collected at different depths; wherein, the concentration of the extract in the organic solution is 0.01 ppm to 1000 ppm, preferably 1 ppm to 100 ppm; and obtaining the TSF Intensity parameter and TSF R1 parameter of the total scanning fluorescence spectrum, wherein the TSF Intensity is the value of the maximum fluorescence intensity in the total scanning fluorescence spectrum, and the TSF R1 is the ratio of the intensity of the fluorescence spectrum at 360 nm to the intensity of 320 nm with an emitting light at 270 nm; a second unit for building a model for interpretation of the oil source rock maturity according to the variation with depth of the TSF Intensity parameter and the TSF R1 parameter obtained by total scanning fluorescence, and identifying the stage of initial oil generation, the stage of major oil generation and the stage of major gas generation; wherein the identification criterion lies in that the initial position of the stage of initial oil generation is set when the increase of the TSF R1 parameter becomes leveling, the initial position of the stage of major oil generation is set when the TSF R1 parameter turns from leveling to decreasing, while the initial position of the stage of major gas generation is set when the TSF Intensity parameter turns from leveling to decreasing; and a third unit for establishing the relationship between the TSF Intensity parameter and/or the TSF R1 parameter with the existing characteristic parameters that quantitatively characterize the maturity of oil source rocks, thereby accomplishing the analysis and determination of the maturity of the oil source rocks.

In the above device for determining maturity in source rocks by total scanning fluorescence, preferably, in the third unit, the process of establishing the relationship between the TSF Intensity parameter and/or the TSF R1 parameter with the existing characteristic parameters that quantitatively characterize the maturity of oil source rocks includes establishing a calibration curve of the TSF Intensity parameter and/or the TSF R1 parameter restricted by the existing characteristic parameters that quantitatively characterize the maturity of the oil source rocks.

In the above device for determining maturity in source rocks by total scanning fluorescence, preferably, the method further includes a fourth unit for establishing a database of calibration curves from different regions so that TSF R1 is directly used as the indication of maturity.

The solution provided by the present disclosure is applicable to a wide range of applications without being limited by the vitrinite content. Moreover, it has advantages including usage of less samples, rapid and simple detection, usefulness in analysis of samples on a large scale, and is also suitable for determination of sample maturity outside the visible fluorescence range.

DETAILED DESCRIPTION

For better understanding of the technical features, the object and the beneficial effects of the present invention, the technical solutions of the present invention are hereinafter described in detail, which is not be construed as limitation to the scope of the present invention.

EXAMPLE 1

Figure 1:
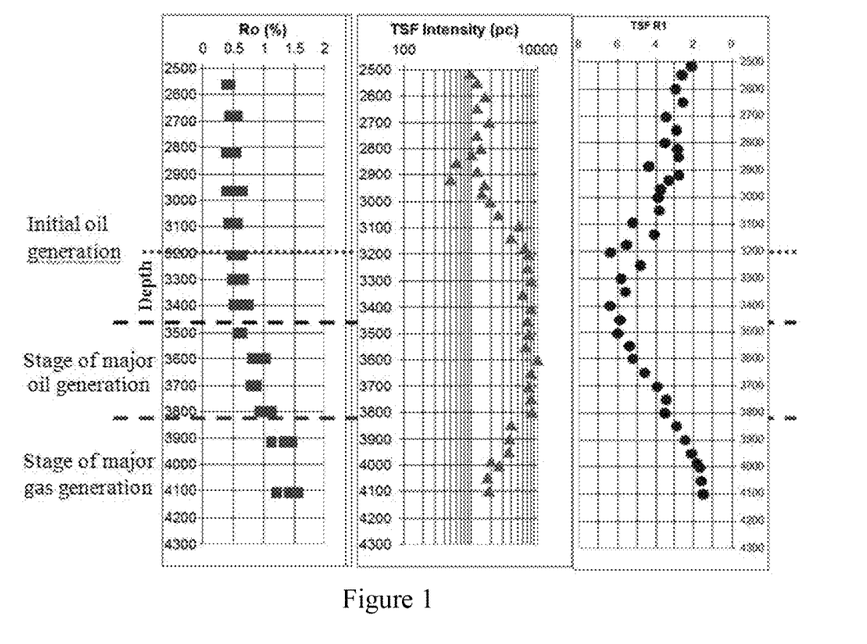
FIG. 1 is a depth plot of the TSF Intensity parameters and TSF R1 parameters in Example 1.
Figure 2A:
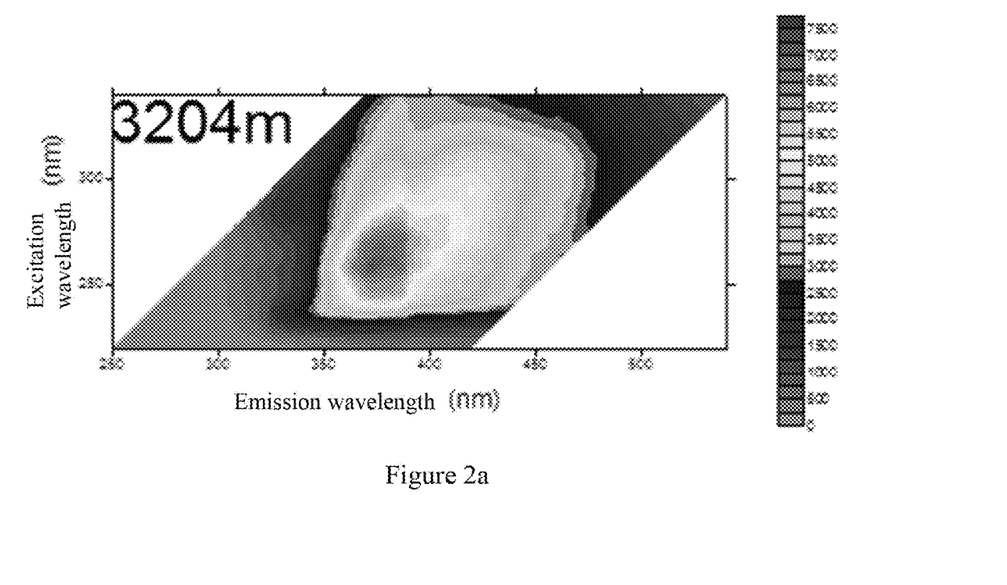
FIG. 2a is the fluorescence spectrum at 3204 m in Example 1.
Figure 2B:
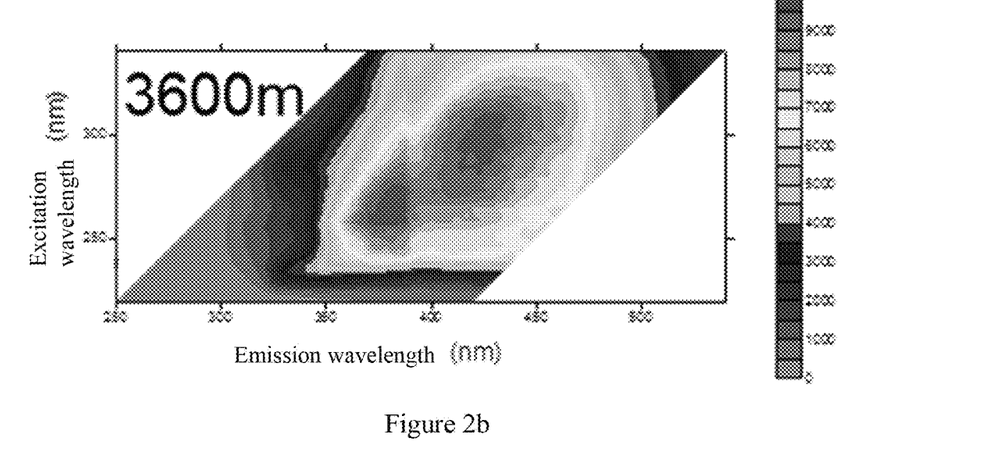
FIG. 2b is the fluorescence spectrum at 3600 m in Example 1.
Figure 2C:
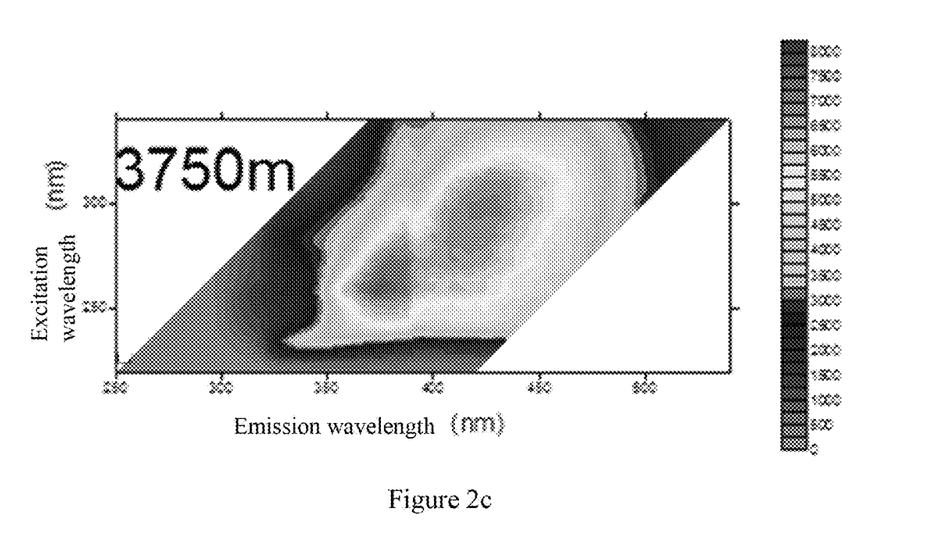
FIG. 2c is the fluorescence spectrum at 3750 m in Example 1.
Figure 2D:
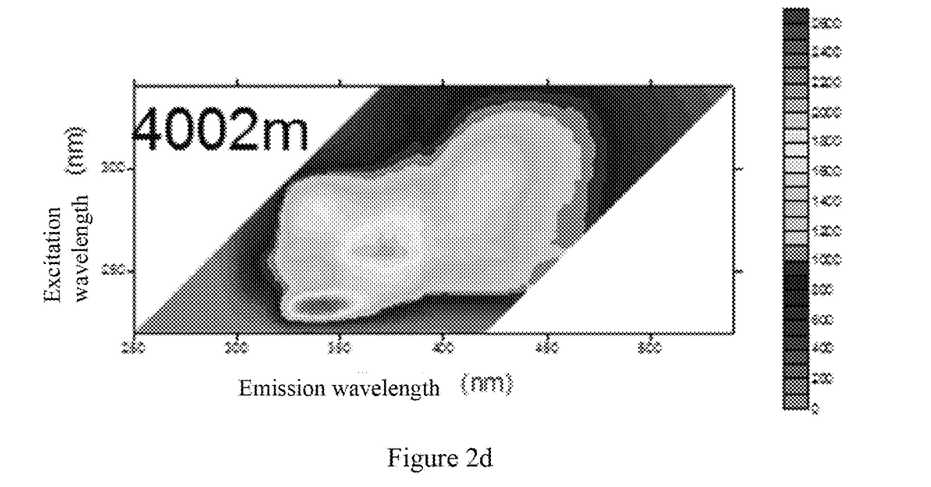
FIG. 2d is the fluorescence spectrum at 4002 m in Example 1.
Figure 3:
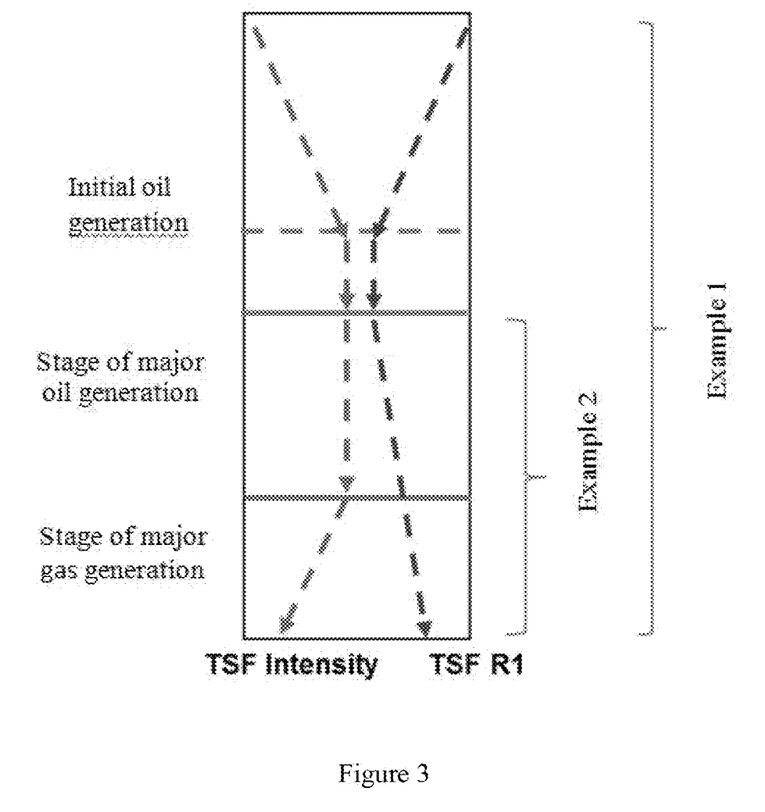
FIG. 3 is the model for interpretation of the maturity results built in Example 1.

The samples in this Example included unknown hydrocarbon source rocks (i.e., hydrocarbon source rocks possibly located before the stage of initial oil generation), and the maturity of oil source rock samples from Australia was determined by the above method of determining thermal maturity of oil source rocks by total scanning fluorescence, using the preferred extract organic solution concentration (1 ppm to 100 ppm), with the specific steps as follows:

(1) obtaining an uncontaminated sample from the sample to be tested, and pulverizing the sample particles to a certain particle size of larger than 120 mesh;

(2) selecting about 0.1 g rock sample to be measured, with the mass measured as $M_r=0.127$ g, adding 10 mL dichloromethane, and ultrasonically extracting for 10 minutes;

(3) standing for 10 minutes, and further ultrasonically extracting for 10 minutes;

(4) standing for 2 h, and transferring $V_1=0.01$ mL into an analysis cuvette, into which 3 mL of organic solvent is added;

(5) placing the analysis cuvette in a fluorescence spectrometer for testing, measuring the TSF Intensity original parameter and TSF R1 parameter of the fluorescence spectrum; and correcting the TSF Intensity original parameter by multiplying by $0.1*3/(M_r \cdot V_1)$ to obtain the TSF Intensity parameter and the TSF R1 parameter;

Primary scanning equipment and parameters: excitation wavelength: 220-340 nm, scanning interval: 10 nm; emission wavelength: 250-540 nm, scanning interval: 5 nm;

(6) repeating steps (1) to (5) for measurement of the next sample; the data from the measurements are shown in Table 1; FIG. 1 is a Bitmap of the parameters, and FIGS. 2a, 2b, 2c, and 2d are fluorescence spectra at 3204 m, 3600 m, 3750 m, and 4002 m, respectively; FIG. 3 is the established model for interpretation;

TABLE 1

Table for the determination of maturity at different depths by total scanning fluorescence

| Depth (m) | Parameter TSF Intensity | Excitation wavelength (nm) | Emission wavelength (nm) | Parameter TSF R1 | Measured Ro (%) | Calculated Ro (%) |
|---|---|---|---|---|---|---|
| 3000 | 6513 | 260 | 380 | 6.4 | / | 0.51 |
| 3177 | 9063 | 258 | 388 | 8.0 | / | 0.22 |
| 3351 | 8950 | 258 | 383 | 6.2 | / | 0.54 |
| 3501 | 9363 | 258 | 383 | 6.0 | 0.60 | / |
| 3552 | 9175 | 298 | 428 | 6.4 | 0.53 | / |
| 3600 | 10000 | 296 | 421 | 6.3 | 0.53 | / |
| 3651 | 10038 | 296 | 426 | 5.3 | / | 0.71 |
| 3702 | 9513 | 294 | 424 | 4.9 | / | 0.78 |
| 3750 | 9438 | 294 | 424 | 4.3 | / | 0.89 |
| 3798 | 9550 | 296 | 426 | 3.9 | 0.83 | / |
| 3849 | 8088 | 296 | 426 | 3.6 | 1.06 | / |
| 3900 | 7975 | 298 | 423 | 3.4 | / | 1.06 |
| 3951 | 7900 | 296 | 426 | 2.4 | / | 1.24 |
| 3990 | 6588 | 296 | 426 | 2.2 | / | 1.28 |
| 4002 | 7188 | 294 | 424 | 2.4 | / | 1.24 |
| 4050 | 6250 | 260 | 375 | 2.1 | 1.35 | / |
| 4098 | 6400 | 232 | 342 | 1.4 | 1.42 | / |
| 4137 | 7900 | 258 | 373 | 2.2 | / | 1.28 |

Figure 4:
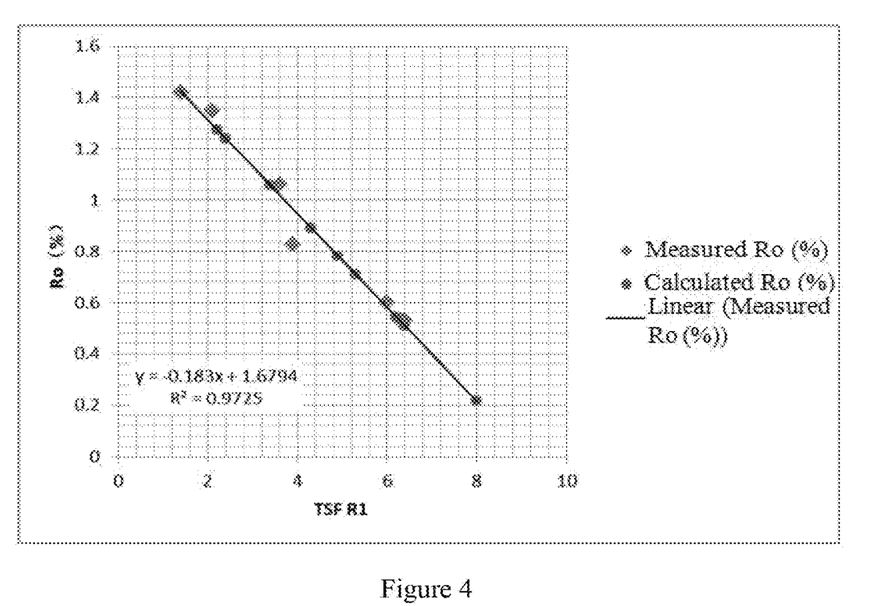
FIG. 4 is a graph showing the relationship between the TSF R1 index of maturity and the vitrinite reflectance in Example 1.

(7) obtaining a calibration curve of the TSF R1 parameter restricted by vitrinite reflectance (see FIG. 4); and (8) calculating the vitrinite reflectance of the samples without $R_o$ measurements by using the calibration curve (see Table 1).

According to the interpretation model of FIG. 3, TSF R1 and TSF Intensity show a good linear relationship, especially TSF R1. Based on the trending curves of these two parameters, the stage of initial oil generation, the stage of major oil generation, and the stage of major gas generation are clearly indicated. Specifically, when the TSF R1 parameter turns from increasing to leveling and the TSF Intensity parameter turns from increasing to leveling, the initial position of the stage of initial oil generation is indicated; when the TSF R1 parameter turns from leveling to decreasing while the TSF Intensity parameter staying at a relative high value, the initial position of the stage of major oil generation is indicated; and when the TSF R1 parameter starts decreasing and the TSF Intensity parameter change from leveling to decreasing, the initial position of the stage of major gas generation is indicated.

EXAMPLE 2

The samples in this Example included a known hydrocarbon source rock (i.e., hydrocarbon source rocks that are already in the stage of initial oil generation). The above method of determining thermal maturity of oil source rocks by total scanning fluorescence was employed to determine the maturity of the known source rock samples (i.e., the hydrocarbon source rocks that are already in the stage of initial oil generation). Higher concentration (0.01 ppm to 1000 ppm) of the extract in the organic solution was appropriate, and the specific steps are as follows:

(1) obtaining an uncontaminated sample from the sample to be tested, and pulverizing the sample particles to a certain particle size of larger than 120 mesh;

(2) selecting about 0.1 g rock sample to be measured, with the mass measured as $M_r$=0.116 g, adding 10 mL dichloromethane, and ultrasonically extracting for 10 minutes;

(3) standing for 10 minutes, and further ultrasonically extracting for 10 minutes;

(4) standing for 2 h, and transferring $V_1$=0.01 mL into an analysis cuvette, into which 3 mL of organic solvent is added;

(5) placing the analysis cuvette in a fluorescence spectrometer for testing, measuring the TSF R1 parameter of the fluorescence spectrum;

Primary scanning equipment and parameters: excitation wavelength: 220-340 nm, scanning interval: 10 nm; emission wavelength: 250-540 nm, scanning interval: 5 nm;

(6) repeating steps (1) to (5) for measurement of the next sample; the data from the measurements are shown in Table 2;

(7) obtaining a calibration curve of the TSF R1 parameter restricted by vitrinite reflectance (see FIG. 5); and (8) with the TSF R1 parameter decreasing as the maturity of the hydrocarbon source rock increases, calibrating the TSF R1 parameter by using parameters such as $R_o$ before the maturity is quantitatively determined, and calculating the maturity of the samples without $R_o$ measurements by using the fitting formula from the calibration curve (see Table 2).

TABLE 2

Table for the measurements of samples with different maturity

| Sample No. | Measured Ro (%) | Parameter TSF R1 | Calculated Ro (%) |
|---|---|---|---|
| Sample 1 | / | 0.965839 | 1.67 |
| Sample 2 | / | 2.26884 | 1.42 |
| Sample 3 | / | 1.58498 | 1.55 |
| Sample 4 | 0.85 | 5.257967 | / |
| Sample 5 | / | 2.639267 | 1.35 |
| Sample 6 | / | 4.872044 | 0.91 |
| Sample 7 | 1.65 | 1.453147 | / |
| Sample 8 | / | 4.629469 | 0.96 |
| Sample 9 | / | 3.902928 | 1.10 |
| Sample 10 | 1.1 | 3.949946 | / |
| Sample 11 | 1.3 | 2.356294 | / |

Figure 5:
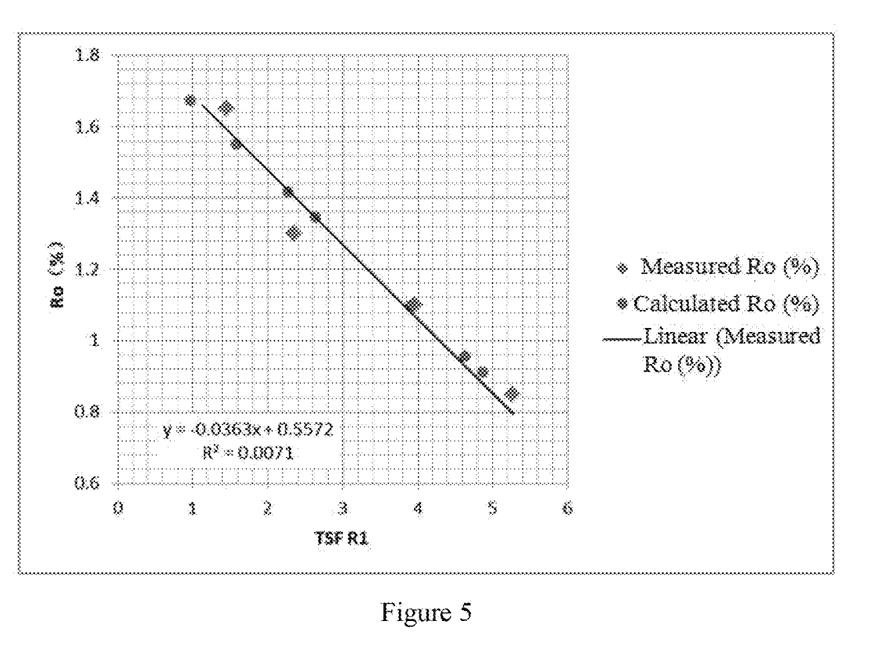
FIG. 5 is a graph showing the relationship between the TSF R1 index of maturity and the vitrinite reflectance in Example 2.

According to the calibration curve in FIG. 5, the parameter TSF R1 shows a good linear relationship. Since samples known to be located at the stage of initial oil generation were tested in this Example, it corresponds to the stage of major oil generation and the stage of major gas generation in the interpretation model in FIG. 3. The linear relationship represented for TSF R1 in this Example also demonstrates the consistence with the corresponding part of the model in FIG. 3. As seen on the basis thereof in connection with FIG. 3, the parameter TSF R1 in this Example shows a good linear relationship and can be used to quantitatively identify the stage of major oil generation and the stage of major gas generation. Specifically, the TSF R1 parameter decreases as the maturity of the hydrocarbon source rock increases, and the TSF R1 parameter, upon calibrating by using parameters such as $R_o$, can be used to quantitatively determine the maturity, and to compare the maturity of different samples; further, by using the fitting formula from the calibration curve, the maturity of the samples is calculated according to the TSF R1 parameter without $R_o$ measurements (see Table 2).

What is claimed is:

1. A method of determining thermal maturity of oil source rocks by total scanning fluorescence, the method comprising:

testing the organic solution of an extract from a series of oil source rock samples collected at different depths by total scanning fluorescence, wherein a concentration of the extract in the organic solution is 0.01 ppm to 1000 ppm; and obtaining TSF Intensity parameters and TSF R1 parameters of the fluorescence spectrum, wherein the TSF Intensity is the value of the maximum fluorescence intensity in the total scanning fluorescence spectrum, and the TSF R1 is the ratio of the intensity at 360 nm to the intensity at 320 nm of the fluorescence spectrum with an emitting light at 270 nm;

building a model for interpretation of the oil source rock maturity according to the variation with depth of the TSF Intensity parameter and the TSF R1 parameter obtained by total scanning fluorescence, and identifying the stage of initial oil generation, the stage of major oil generation and the stage of major gas generation; wherein the identification criterion lies in that the initial position of the stage of initial oil generation is set when the increase of the TSF R1 parameter becomes leveling, the initial position of the stage of major oil generation is set when the TSF R1 parameter turns from leveling to decreasing, and the initial position of the stage of major gas generation is set when the TSF Intensity parameter turns from leveling to decreasing; and establishing the relationship between the TSF Intensity parameter and/or the TSF R1 parameter with existing characteristic parameters that quantitatively characterize the maturity of oil source rocks, thereby accomplishing the analysis and determination of the maturity of the oil source rocks.

2. The method of claim 1, wherein the concentration of the extract in the organic solution is 1 ppm to 100 ppm.

3. The method of claim 1, wherein establishing the relationship between the TSF Intensity parameter and/or the TSF R1 parameter with the existing characteristic parameters for quantitatively characterize the maturity of oil source rocks comprises establishing a calibration curve of the TSF Intensity parameter and/or the TSF R1 parameter restricted by the existing characteristic parameters that quantitatively characterize the maturity of the oil source rocks.

4. The method of claim 3, further comprising establishing a database of calibration curves from different regions so that TSF R1 is directly used as the indication of maturity.

5. The method of claim 1, wherein the existing characteristic parameters that quantitatively characterize the maturity of oil source rocks include vitrinite reflectance, rock pyrolysis, the degree of spore-pollen carbonization, or thermal alteration index.

6. The method of claim 1, wherein the existing characteristic parameter that quantitatively characterizes the maturity of the oil source rocks is vitrinite reflectance.

7. The method of claim 1, wherein the process of preparing the organic solution of the extract comprises pulverizing the sample to be tested with the mass of $M_r$, adding the organic solvent, and ultrasonically extracting at least twice; and diluting to the preset concentration after extraction to prepare the organic solution of the extract.

8. The method of claim 7, wherein the process of preparing the organic solution of the extract comprises:
- obtaining an uncontaminated sample from the sample to be tested, and pulverizing the sample particles to a certain particle size;
- selecting a rock sample to be measured with the mass of $M_r$, adding 10 mL organic solvent, and ultrasonically extracting for 10 minutes, wherein $M_r$ is in the range of 0.1 g-1.0 g;
- standing for 10 minutes, and further ultrasonically extracting for 10 minutes;
- standing for a certain period of time, and transferring $V_1$ mL into an analysis dish, into which 3 mL of the organic solvent is added, wherein $V_1$ is in the range of 0.001 mL-0.1 mL; and
- placing the analysis dish in a fluorescence spectrometer for testing, measuring the TSF Intensity original parameter and TSF R1 parameter of the fluorescence spectrum; and correcting the TSF Intensity original parameter by multiplying by $0.1*3/(M_r \cdot V_1)$ to obtain the TSF Intensity parameter.

\* \* \* \* \*